(12) United States Patent
Gibson et al.

(10) Patent No.: US 7,236,566 B2
(45) Date of Patent: Jun. 26, 2007

(54) IN-SITU X-RAY DIFFRACTION SYSTEM USING SOURCES AND DETECTORS AT FIXED ANGULAR POSITIONS

(76) Inventors: David M. Gibson, 526 New Salem Rd., Voorheesville, NY (US) 12188; Walter M. Gibson, 790 Cass Hill Rd., Voorheesville, NY (US) 12186; Huapeng Huang, 6 Sable Ter., Latham, NY (US) 12110

(*) Notice: Subject to any disclaimer, the term of this patent is extended or adjusted under 35 U.S.C. 154(b) by 0 days.

(21) Appl. No.: 11/346,699

(22) Filed: Feb. 3, 2006

(65) Prior Publication Data
US 2006/0140343 A1    Jun. 29, 2006

Related U.S. Application Data

(63) Continuation of application No. PCT/US04/25112, filed on Aug. 4, 2004.

(60) Provisional application No. 60/492,400, filed on Aug. 4, 2003.

(51) Int. Cl.
*G01N 23/20* (2006.01)
*G21K 1/06* (2006.01)

(52) U.S. Cl. .................. 378/71; 378/72; 378/76; 378/84; 378/85

(58) Field of Classification Search ........ 378/70, 378/71, 72, 73, 75, 76, 79, 80, 81, 86, 88, 378/89, 90, 84, 85
See application file for complete search history.

(56) References Cited

U.S. PATENT DOCUMENTS

| | | | |
|---|---|---|---|
| 3,596,092 A * | 7/1971 | Marjoram | 378/71 |
| 3,639,758 A * | 2/1972 | Shimura | 378/72 |
| 3,639,760 A * | 2/1972 | Mizunuma | 378/72 |
| 3,759,383 A * | 9/1973 | Inoue | 209/589 |
| 3,833,810 A * | 9/1974 | Efanov et al. | 378/74 |
| 3,868,506 A * | 2/1975 | Ogiso | 378/72 |
| 4,649,556 A | 3/1987 | Rinik et al. | 378/71 |
| 4,686,631 A * | 8/1987 | Ruud | 378/72 |

(Continued)

FOREIGN PATENT DOCUMENTS

WO    WO 05/010512 A1    2/2005

*Primary Examiner*—Allen C. Ho
(74) *Attorney, Agent, or Firm*—Jeffrey R. Klembczyk, Esq.; Kevin P. Radigan, Esq.; Heslin Rothenberg Farley & Mesiti, P.C.

(57) ABSTRACT

An x-ray diffraction technique for measuring a known characteristic of a sample of a material in an in-situ state. The technique includes using an x-ray source for emitting substantially divergent x-ray radiation—with a collimating optic disposed with respect to the fixed source for producing a substantially parallel beam of x-ray radiation by receiving and redirecting the divergent paths of the divergent x-ray radiation. A first x-ray detector collects radiation diffracted from the sample; wherein the source and detector are fixed, during operation thereof, in position relative to each other and in at least one dimension relative to the sample according to a-priori knowledge about the known characteristic of the sample. A second x-ray detector may be fixed relative to the first x-ray detector according to the a-priori knowledge about the known characteristic of the sample, especially in a phase monitoring embodiment of the present invention.

18 Claims, 13 Drawing Sheets

U.S. PATENT DOCUMENTS

| | | | |
|---|---|---|---|
| 5,125,016 A * | 6/1992 | Korhonen et al. | 378/72 |
| 5,148,458 A | 9/1992 | Ruud | 378/72 |
| 5,155,751 A * | 10/1992 | Chohata et al. | 378/71 |
| 5,192,869 A | 3/1993 | Kumakhov | 250/505.1 |
| 5,276,724 A * | 1/1994 | Kumasaka et al. | 378/34 |
| 5,497,008 A * | 3/1996 | Kumakhov | 250/505.1 |
| 5,553,105 A | 9/1996 | Xiao | 376/159 |
| 5,570,408 A * | 10/1996 | Gibson | 378/145 |
| 5,744,813 A * | 4/1998 | Kumakhov | 250/505.1 |
| 5,745,547 A * | 4/1998 | Xiao | 378/145 |
| 5,784,432 A | 7/1998 | Kurtz et al. | 378/70 |
| 5,812,631 A * | 9/1998 | Yan et al. | 378/85 |
| 5,828,724 A * | 10/1998 | Kurtz | 378/70 |
| 6,266,392 B1 * | 7/2001 | Fujinawa et al. | 378/149 |
| 6,271,534 B1 * | 8/2001 | Kumakhov | 250/505.1 |
| 6,301,330 B1 | 10/2001 | Kurtz et al. | 378/71 |
| 6,353,656 B1 * | 3/2002 | LeVert et al. | 378/72 |
| 6,493,420 B2 * | 12/2002 | Ruud | 378/72 |
| 6,697,454 B1 * | 2/2004 | Nicolich et al. | 378/85 |
| 6,754,304 B1 * | 6/2004 | Kumakhov | 378/45 |
| 6,850,593 B1 * | 2/2005 | Tamura | 378/49 |
| 2002/0003859 A1 | 1/2002 | Kogan | 378/84 |
| 2002/0174918 A1 * | 11/2002 | Fujimura et al. | 148/508 |

* cited by examiner

IN-SITU X-RAY DIFFRACTION SYSTEM USING SOURCES AND DETECTORS AT FIXED ANGULAR POSITIONS

RELATED APPLICATION INFORMATION

This application is a continuation of PCT Application PCT/US2004/025112 filed Aug. 4, 2004, and published under the PCT Articles in English as WO 2005/031329 A1 on Apr. 7, 2005. PCT/US2004/025112 claimed priority to U.S. Provisional Application No. 60/492,400, filed Aug. 4, 2003. The entire disclosures of PCT/US2004/025112 and U.S. Ser. No. 60/492,400 are incorporated herein by reference in their entirety.

GOVERNMENT RIGHTS STATEMENT

This invention was made with Government support under Contract #: DE-FG02-99ER82918 awarded by the United States Department of Energy to X-Ray Optical Systems, Inc. The Government has certain rights in this invention.

TECHNICAL FIELD

This invention relates in general to x-ray diffraction. More particularly, the present invention relates to a technique for x-ray diffraction utilizing fixed sources and detectors, aligned along axes pre-determined according to the properties of the material under measurement.

BACKGROUND OF THE INVENTION

X-ray analysis techniques have been some of the most significant developments in twentieth-century science and technology. The use of x-ray diffraction, spectroscopy, imaging, and other x-ray analysis techniques has led to a profound increase in knowledge in virtually all scientific fields.

One existing class of surface analysis is based on diffraction of x-rays directed toward a sample. The diffracted radiation can be detected and various physical properties, including crystalline structure and phase, and surface texture, can be algorithmically determined. These measurements can be used for process monitoring in a wide variety of applications, including the manufacture of semiconductors, pharmaceuticals, specialty metals and coatings, building materials, and other crystalline structures.

Conventionally, this measurement and analysis process required the detection of diffracted x-ray information from multiple locations relative to the sample in a laboratory environment. Conventional diffraction systems are large, expensive and prone to reliability problems. Their size, cost, and performance limit their use to these off-line "laboratory" settings.

There is a strong drive in the market for applying this technology to real-time process monitoring—allowing real-time process control. In many manufacturing environments, real-time process monitoring and feedback eliminates the need to transport samples to a lab to undergo testing. Real-time process monitoring enables immediate corrective measures, without waiting for laboratory results while an unsatisfactory product continues to be manufactured.

These types of real-time measurements present certain practical concerns not encountered in laboratory settings—such as the need for smaller, more reliable instruments; and for sample handling and excitation/detection techniques compatible with the surrounding production environment. For example, the sample may be continuously moving past the instrument on a movement path. The technique must be compatible with both the sample movement and the movement path.

In "bypass" configurations (where sample(s) from the production line may be diverted to proximate measurement stations)—stringent sample preparation is not practicable. The measurement technique must accommodate the sample "as is" and without any undue preparation.

An instrument must be small enough for installation into a manufacturing environment without impacting the surrounding production equipment. In general, the system must be smaller and simpler than most conventional x-ray diffraction systems, but with similar performance characteristics.

Such measurement environments, however, also offer certain benefits that often do not exist in laboratory environments. For example, the specific type of material under study is usually known; as is the specific material property of interest (e.g., phase or texture). The movement paths are also known, as are the material sampling and handling techniques.

What is required, therefore, are techniques, methods and systems which exploit the benefits of x-ray diffraction measurements in real-time production environments; which can endure the demanding conditions of these environments; and which also capitalize on some of the a-priori information associated with these environments.

SUMMARY OF THE INVENTION

The shortcomings of the prior art are overcome and additional advantages are provided through the present invention which in one aspect is an x-ray diffraction technique (apparatus, method and program products) for measuring a known characteristic of a sample of a material in an in-situ state. The technique includes using an x-ray source for emitting substantially divergent x-ray radiation—with a collimating optic disposed with respect to the fixed source for producing a substantially parallel beam of x-ray radiation by receiving and redirecting the divergent paths of the divergent x-ray radiation. The first x-ray detector collects radiation diffracted from the sample; wherein the source and detector are fixed, during operation thereof, in position relative to each other and in at least one dimension relative to the sample according to a-priori knowledge about the known characteristic of the sample. A second x-ray detector may be fixed relative to the first x-ray detector according to the a-priori knowledge about the known characteristic of the sample, especially in a phase monitoring embodiment of the present invention. Angular filters can be affixed to the first and/or second x-ray detector for limiting the angles from which the diffracted radiation is collected by the detector. Fixed source/detector pairs can be employed in texture measurement embodiments of the present invention.

Compact, low power sources can be used, along with collimating polycapillary optics, to enhance the in-situ performance of these techniques.

The a-priori knowledge regarding the sample characteristics of interest allows fixation of the sources and detectors with respect to each other and the sample, thereby simplifying system design, by eliminating the need for scanning.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION OF THE INVENTION

The present invention is directed to an x-ray system having detectors fixed in position according to certain known, a-priori information about the sample under study and its movement path, in an "in-situ" production environment. The term "in-situ" as used herein connotes applications where the sample exists in its own environment, including under active production. Examples include an "in-line" system, coupled directly to a production line and analyzing material as it exists (possibly moving) in the production line in a substantially predictable state; or an "at-line" system which is closely associated with the production line, but which analyzes samples removed from their production line with minimal sample preparation prior to measurement; or an "on-site" system which can be portably transported to a site at which the sample resides in a substantially predictable state; but generally exclude "off-line," fixed laboratory environments. The term "production" herein connotes active production or transformation of a material in a production facility, including reviewing materials in their native state (i.e., at an ore mine) at the time their initial transformation occurs.

Figure 1A:
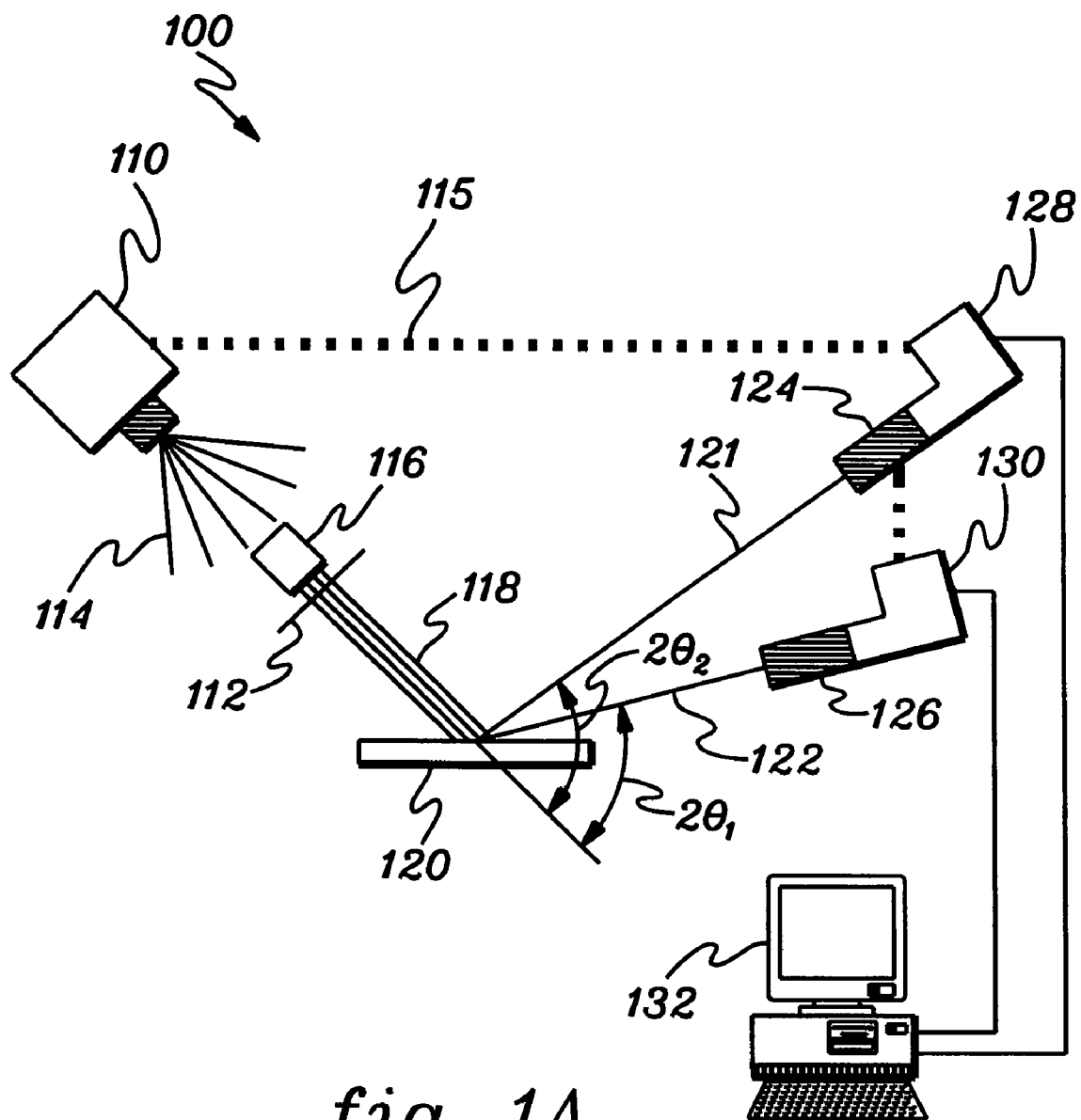
FIGS. 1a-b depict front and top perspective views of a phase monitoring, x-ray diffraction system with a source and two detectors fixed in position at 2 different "2θ" directions, in accordance with an aspect of the present invention.
Figure 1B:
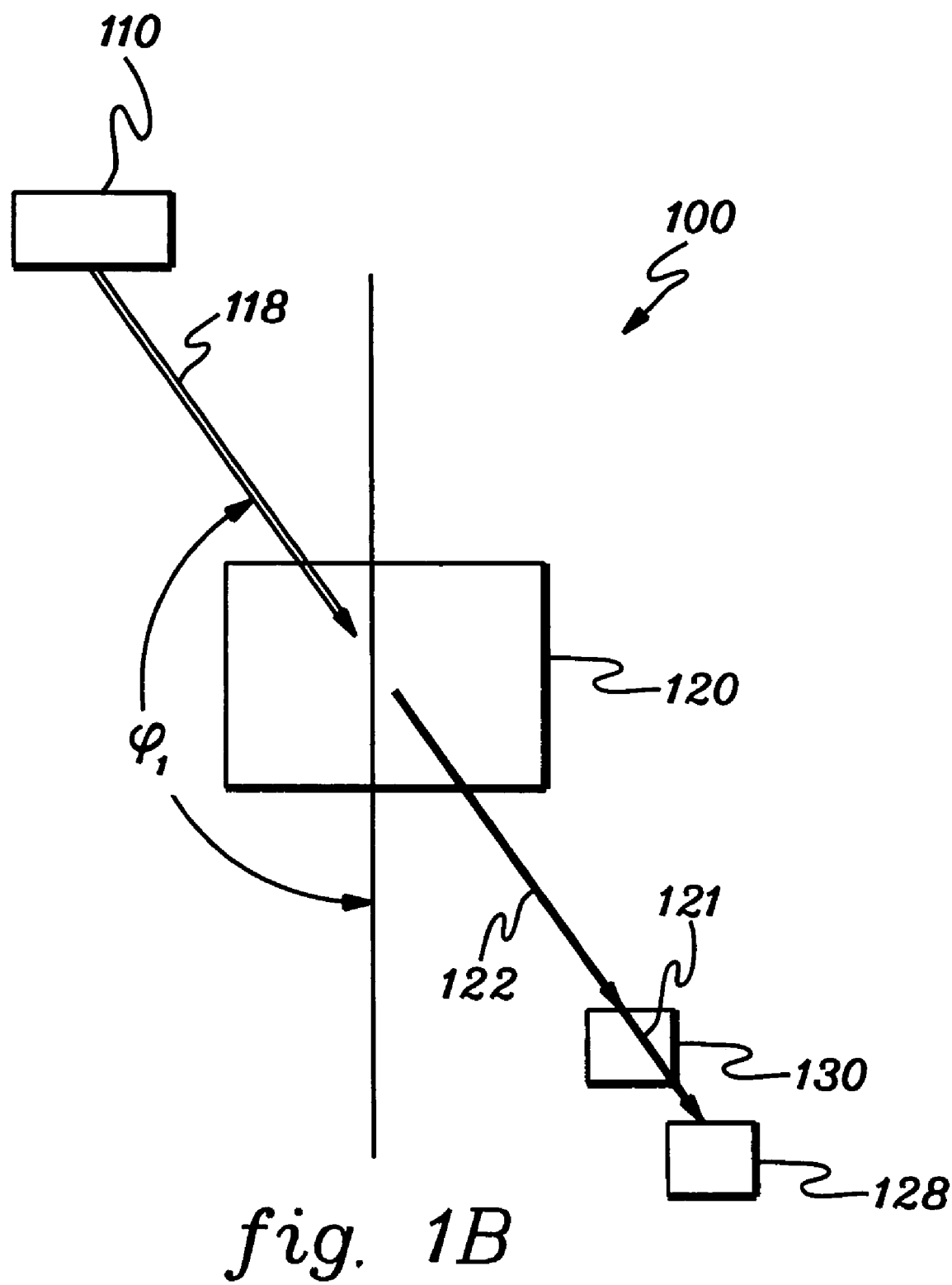

The "in-situ" applications of the present invention generally imply that sample 120 is a material that has some characteristic from which a-priori knowledge can be derived to optimize the XRD system of the present invention. For example, certain crystalline structure information might be known, enabling crystalline phase monitoring using two different detectors at different 2-theta angles. This is discussed further below regarding the "steel phase" example. As another example, crystalline orientation information might be assumed, any changes in which would enable surface texture monitoring using two different source/detector pairs at different phi angles. The configuration of FIGS. 1a-b shows a single source 110, and two fixed detectors at the 2-theta angles $2\theta_1$ and $2\theta_2$, for phase monitoring. This is discussed further below in the "texture sensing" example.

Phase monitoring embodiments of the present invention:

FIGS. 1a-b depict front and top perspective views of a phase monitoring, x-ray diffraction (XRD) system 100 in accordance with the present invention including a source 110, a shutter 112, diverging x-rays 114, a collimating optic 116, a parallel beam 118, a sample 120, diffracted beams 121/122, a first angular filter 124, second angular filter 126, a detector 128, a detector 130, a rigid support structure 115 and a computer 132.

Source 110 and collimating optic 116 provide x-ray radiation in the form of a parallel beam 118. Particular details of an exemplary source/optic combination in accordance with the present invention are discussed in connection with FIGS. 6a-c below. Source 110 may be a point source that generates the divergent x-rays 114 from a small spot and emits the divergent x-rays 114 isotropically from that small spot, or may be a large area source that generates x-rays over a relatively large area and emits the divergent x-rays 114 over a range of angles from each position on the source 110. The divergent x-rays 114 may be emitted from an x-ray tube resulting from electron bombardment of an anode, with divergent x-rays 114 constantly emitted from the source, such as an Oxford 5011 electron bombardment source.

The collimating optic 116 is a device capable of producing a beam of sufficient parallelism to generate a usable diffraction pattern. Parallel beams are also less susceptible to sample displacement in the vertical direction—a significant advantage when operating in an in-situ environment. Collimating optic 116 may be a soller slit collimator, which is an array of absorbing plates separated by gaps. However, since a Sollar slit is a blocking method and hence inherently inefficient, a large source may be required. A pinhole collimator is also possible, but that is also an inefficient technique.

Other collimating optics are preferred, i.e., those which receive a wide angle of divergent x-rays and redirect the divergent rays into a parallel beam. Such optics include, for example, curved crystal optics (see e.g., X-Ray Optical, Inc. U.S. Pat. Nos. 6,285,506 and 6,317,483—all of which are incorporated by reference herein in their entirety), multilayer optics, or polycapillary optics.

Therefore, the collimating optic 116 may be a polycapillary optic—a bundle of thin, hollow tubes that collects a portion of the diverging x-rays 114 over a significant solid angle, transmits and therefore redirects the photons from their otherwise straight paths via total external reflection inside the channels, and collimates the collected divergent x-rays 114 into a parallel beam 118 directed at the sample 120. This enables the use of smaller, low-power sources. Again, the optic/source combination optimized for use in the systems herein are discussed in connection with FIGS. 6a-c below.

The system 100 may further include a shutter 112, to block the entirety of the parallel beam 118, when desired.

Angular filters enable more precise control over the diffracted radiation detected by detectors 128 and 130. The first angular filter 124 and the second angular filter 126 may be polycapillary optics (see the discussion below regarding FIG. 7) that reject radiation incident outside of a critical angle for total external reflection while efficiently transmitting radiation within the critical angle, towards the detectors 128 and 130, respectively. In one enhanced embodiment of the present invention, the resolution of the angular filters is determined according to the peak width of the diffraction peak being monitored. By correlating the angular resolution of the angular filter to the peak width, the maximal power from the peak is provided to the detector, while minimizing any background noise from the off-peak areas. Alternately, soller slits may comprise the angular filters 124 and 126. One- and two-dimensional variants of these filters may also be used.

The detectors 128 and 130 are elements that collect the diffraction pattern produced by the diffracted beams 121 and 122 (each along its own respective 2-theta angle chosen according to a-priori knowledge about the sample characteristics under study) respectively and produce output signals that vary with changes in the diffracted x-rays incident upon them and are communicated to the computer 132. The detectors 128 and 130 may be scintillation detectors, detectors that consist of a photomultiplier tube facing a region that contains a solid material such as sodium iodide laced with thallium atoms. Alternately, detector 130 could be a semiconductor detector. These types of "point" detectors are preferred. Other detectors are known to those skilled in the art.

Detectors used in the disclosed in-situ XRD system usually need to be of small size for compact design of the whole system, and have some moderate resolution (<1 kev) to select the x-ray source Ka radiation. Higher energy resolutions (which may require the detector to be cooled with liquid nitrogen) are usually not needed. The detectors may require high counting efficiency, and the resultant high sensitivities to detect the diffraction beam, which may be weak. A large capture area (combined with a large angular filter) is desired for a larger tolerance of sample position displacement.

The present invention makes use of small, inexpensive "point detectors" in one embodiment. One example includes a detector (used for texture measurement) with 25 mm$^2$ capture area and ~200 ev energy resolution. A gas proportional counter detector may be used for steel phase monitoring, with 12×25 mm$^2$ capture area and ~1000 ev energy resolution.

A rigid support structure 115 supports the source and detectors in fixed position to each other (while measurements are taken) and the entire system is placed in a measurement position relative to the underlying sample 120. The system can be fixed with respect to the sample, or can hover over the sample, or the sample can move under the fixed system. For phase monitoring, the system can rotate with respect to the sample. For texture monitoring, the rotational (phi) angle must be fixed. In general though, at least one dimension must be fixed between the sample and the system to ensure accurate measurements. This dimension is usually the distance between the system and the sample.

The computer 132 is a data acquisition device that may contain a standard analysis software package. The computer serves to analyze, interpret, and display information about the sample 120 from the response of the detectors 128 and 130 to the diffraction patterns at their respective 2-theta angles.

The top view of FIG. 1a shows the source 110, detector 128 and detector 130 aligned in parallel along the same phi angle, $\phi_1$. However, the offset between the detectors can be in the theta direction, the phi direction (discussed below in connection with FIGS. 2a-b), the chi direction (i.e., the plane formed by the source/detector pair) or any combination of these directions.

In operation, the x-ray diffraction system 100 provides an in-situ system that enables, e.g., phase detection or monitoring and quantitative analysis of the sample 120. The x-ray diffraction system 100 is particularly well suited for in-situ phase analysis of a moving media (e.g., moving galvanized steel in a manufacturing environment subsequent to the application of a coating to the sample 120—see discussions below). The low power source 110 emits the diverging x-rays 114, which are collimated into the parallel beam 118 by the collimating optic 116. The parallel beam 118 of x-rays impinges upon the sample 120 and is diffracted by the crystalline phases in the sample 120 according to Bragg's Law ($n\lambda=2d \sin\theta$, where d is the spacing between atomic planes in the crystalline phase, n is an integer, $\theta$ is the angle of incidence, and $\lambda$ is the wavelength of the incident x-ray), and thereby generates the diffracted beams 121 and 122. The intensity of the x-rays within the diffracted beams is measured as a function of the diffraction angle $2\theta$. This diffraction pattern may be used in this example to identify and monitor the crystalline phases and other structural properties of the sample 120.

In the case where the diffraction angle of a specific phase is known, the diffraction pattern detection devices can be placed in fixed position. As such, two detectors 128 and 130, with the angular filters 124 and 126, respectively, are included in the present invention to acquire data from two different diffraction angles, and $2\theta_2$ and $2\theta_1$, respectively. The detector 130 measures the intensity of x-ray radiation directed to it by the second angular filter 126 within a preselected energy window from an angle 201. This obtains "background" information from a region in which there is expected to be no diffraction peak, while the detector 128 measures the intensity of x-ray radiation directed to it by the first angular filter 124 within a preselected energy window from an angle $2\theta_2$, a region in which the desired phase diffraction peak is expected to appear. An algorithm is performed and a ratio is obtained by the signals input from the detectors 128 and 130 to the computer 132 and the amount of a given phase is determined. In the case that none of a given phase is present, the counts in the region of interest for the diffracted beam 121 at an angle $2\theta_2$ received at the detector 128 is the same as the counts in the background measured at detector 130, yielding a ratio of one to one. As the amount of the given phase increases, this ratio becomes greater than one, and an accurate determination of the percentage of that phase present in the sample 120 can be made.

The present invention is especially useful in applications where a single material phase needs to be examined, such as detection of unwanted phase change in steel that has undergone a galvanizing process, and the angular positions of the diffraction peaks are known with some degree of accuracy. Using the two fixed detectors 128 and 130 (with the optional angular filters 124 and 126) instead of either a scanning, movable detector significantly reduces the size and complexity of the detector assembly in an x-ray diffraction system. This results in both lower cost and increased reliability, which are especially important for in-situ applications.

The inclusion of the collimating optic 116 produces the parallel beam 118 of sufficient intensity to accomplish the desired measurements in a time frame that enables immediate feedback while utilizing the low power source 110. Conventional x-ray diffraction systems used for crystallinity analysis make use of a focussing geometry called Bragg-Brentano, in which extensive polishing and sample preparation, as well as sample scanning is often necessary. The parallel beam 118 utilized in the present invention eliminates the need for significant sample preparation, and scanning during operation. Scanning may be done once, to determine the shape of the scan curves and ultimate angular position of the detectors. Then during operation, no scanning is necessary. The elimination of the need for sample scanning during operation further enables a reliable compact x-ray diffraction system 100 that may used for inline process control by eliminating the need for a sophisticated sample control system. It should be noted that the use of high-efficiency polycapillary or curved optics for collimating optic 116 allows for both higher intensity beams (shorter measurement times) and smaller, lower cost, low power x-ray sources.

Figure 2A:
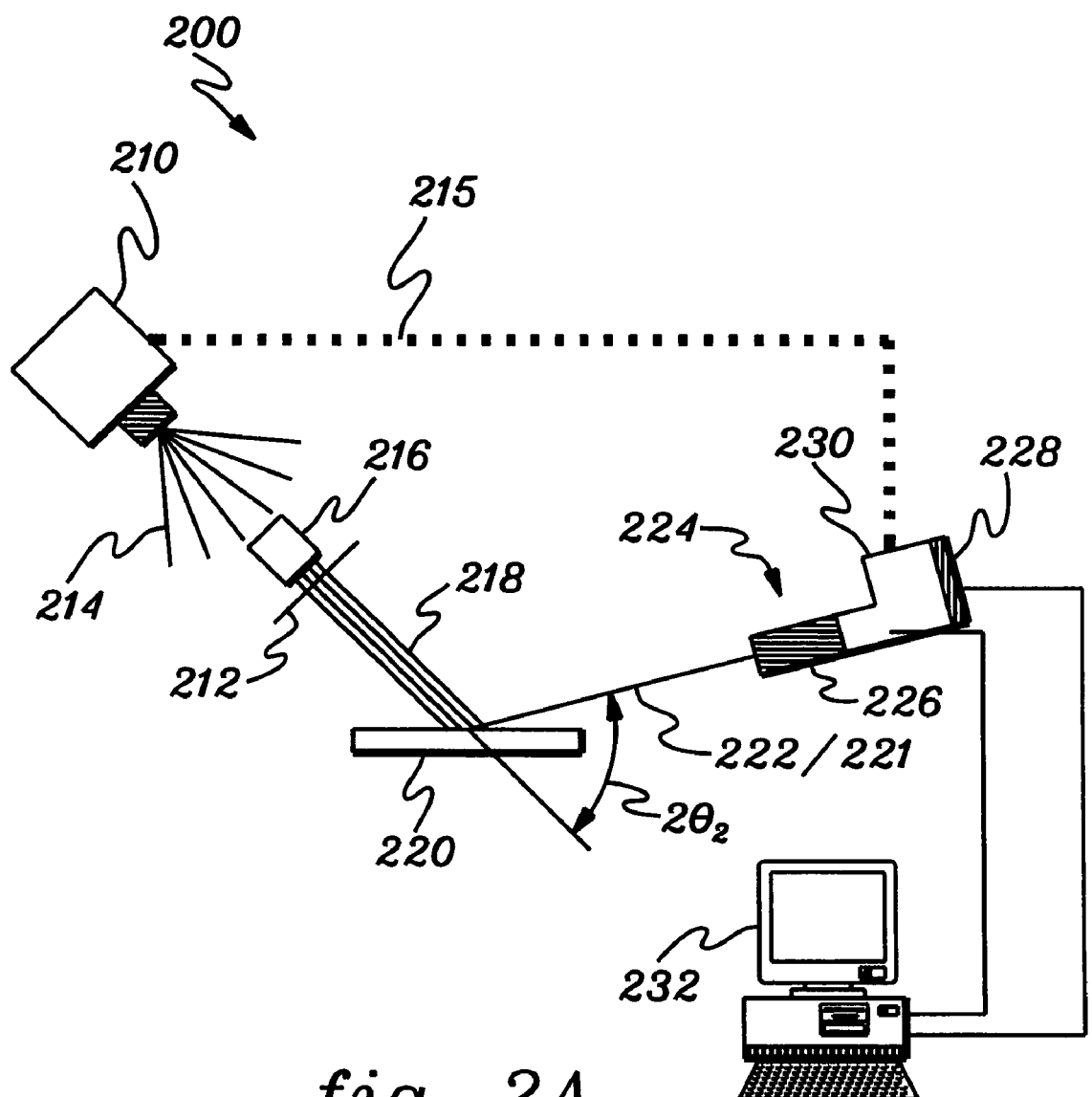
FIGS. 2a-b depict top and perspective views of another monitoring, x-ray diffraction system with a source and two detectors fixed in position at 2 different "φ" directions, in accordance with another aspect of the present invention.
Figure 2B:
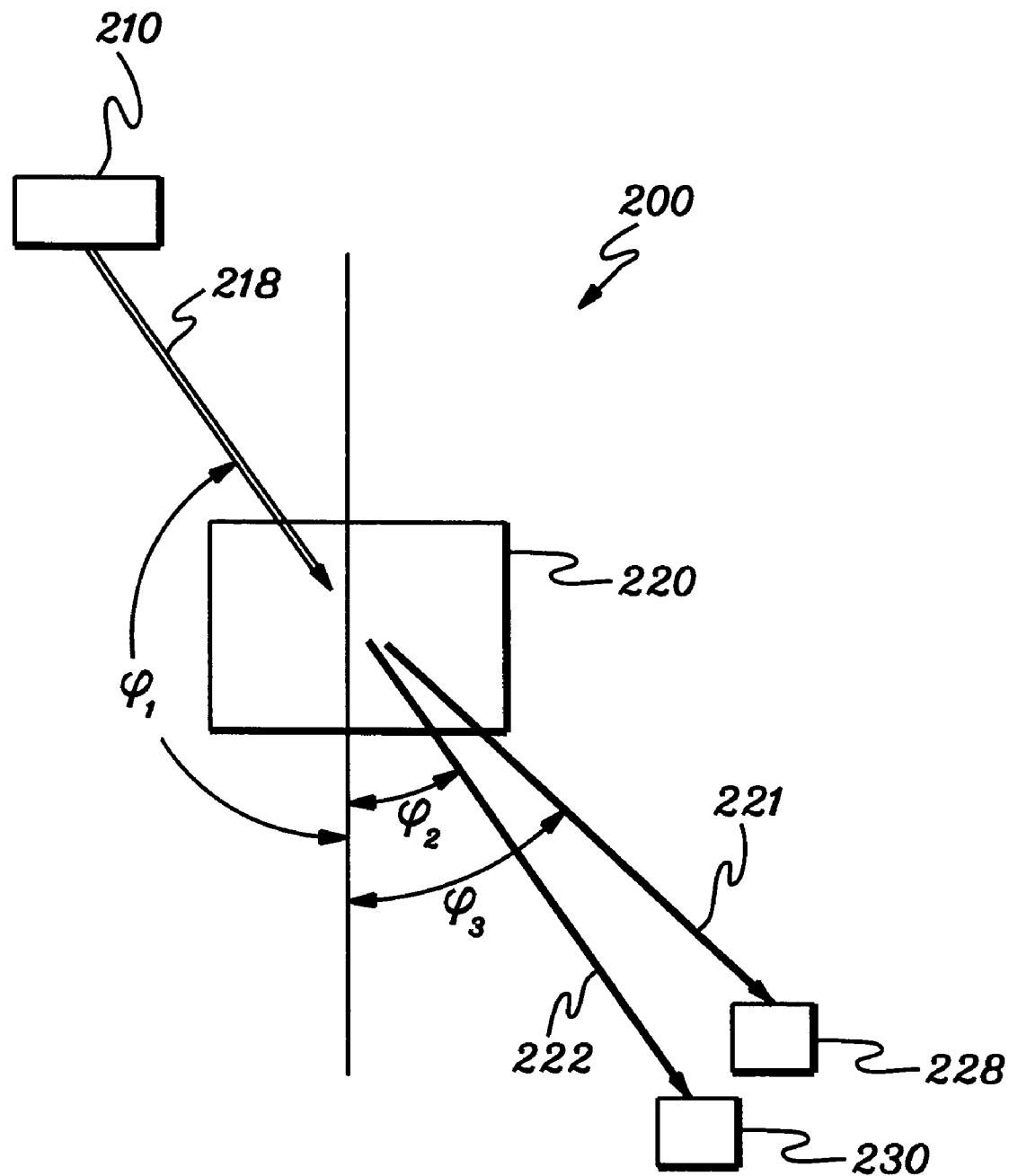

While this preferred embodiment includes the use of two fixed detectors (one at peak and one at background), other detector configurations are possible. A single detector could be positioned at the diffraction peak (assuming the locale of the peak and the background noise level can be predicted with some degree of accuracy). More than two detectors can be used at any number of positions around the diffraction, for example, two on background, two along the sides of the peak, and a single at the peak—for a total of five (see the discussion below regarding FIG. 8). FIGS. 2a-b show an x-ray diffraction system similar to that of FIGS. 1a-b with the angular positions of the fixed detectors at the same 2-theta angle, but varied in the phi direction. FIGS. 2a-b depict an x-ray diffraction (XRD) system 200 in accordance with the present invention including a source 210, a shutter 212, diverging x-rays 214, a collimating optic 216, a parallel beam 218, a sample 220, diffracted beams 221/222, a first angular filter 224 (not entirely visible), second angular filter 226, a detector 228, a detector 230, a rigid support structure 215 and a computer 232.

These components can be similar to those discussed above with respect to FIGS. 1a-b, but are simply arranged at different angular positions. The position of the detectors can be displaced along the 2-theta position (FIGS. 1a-b), displaced along the phi position (FIGS. 2a-b) or a combination of both directions (not shown) depending on the application and the type and quality of the information known a-priori about the potential application.

Steel Phase Monitoring Application:

One example of the use of the present invention involves the real-time, in-situ analysis of steel sheets under production. Hot dip galvannealed steel sheets have excellent corrosion resistance, paintability, phosphatability and weldability; and the properties of these steels are therefore in high demand in the automotive industry. It is important for producing galvannealed steel sheets with superior press formability such as drawability and anti-powdering behavior to control the microstructure of galvannealed coatings. The coating properties are greatly influenced by the composition and the microstructure of the coating layer that is formed on the steel substrate during the hot dip galvanizing and galvannealing processes.

For the hot dip galvannealing process a zinc bath modified with aluminum is used. In the Zn bath, a Fe—Al—Zn reaction initially takes place at the interface between the steel substrate and the zinc coating, which obstructs the Zn—Fe reaction. This step is called inhibition. To initiate the Zn—Fe reaction, it is necessary to remove the interface layer, the thickness of which increases with increasing aluminum content in the Zn-bath. A first Fe—Zn alloying reaction occurs during the formation of the intermetallic $\zeta$-phase, columnar $\zeta$-crystals grow on top of the thin Fe—Al. During subsequent Zn—Fe reactions the local formation of $\zeta$-phase and of another intermetallic $\delta$-phase in form of polygonal crystals begins on the surface of the steel substrate and then spreads across the entire interface layer. After the initial solid/liquid reaction step (solid Iron, Zn—Fe phases and liquid Zn), subsequent solid state reactions occur, transformation of $\zeta$-phase to $\delta$-phase and growth of $\Gamma$-phase. The quality of the Zn—Fe layer is mainly influenced by several parameters: the steel substrate, the iron content, and the optimum distribution of the Zn—Fe phases in the coating. The second two parameters are determined mainly by the temperature and holding time in the galvannealing furnace, the Al content in the Zn bath, steel composition and the steel surface conditions.

If not produced properly, galvanneal steel can exhibit powdering or flaking, due to $\Gamma$-phase formation between the steel substrate and the galvanneal surface coating. This causes the loss of coating from the steel surface, which occurs during forming operations. Forming processes in the automotive industry set high standards towards the certification of the steel grade. The phase formation process in the surface layer is a complex process and producing the right steel grade at a high yield can be challenging. The individual steel mills have to certify their products before shipping. Therefore, an in-line monitoring system capable of identifying and monitoring phases will greatly benefit a continuous sheet steel galvannealing line. In addition, a semi-quantitative analysis will give nearly real-time results on formation trends as the galvannealed steel sheets roll by the diffraction system.

The phase composition, or the amounts of each iron zinc compound in the coating is a very important component of galvanneal steel and is directly related to the flaking of the coating. This results in a close connection between the alloying degree of the coating and the press formability of the hot dip galvannealed steel sheet. When a thick $\zeta$-phase remains on the surface of the coating, this indicates a low alloying degree of coating. The surface dynamic friction of the coating increases resulting in the poor drawability and rupture of steel sheets. Conversely, when the alloying degree goes up and thickness of the $\Gamma$-phase increases the powdering phenomena becomes noticeable. To produce hot dip galvannealed steel sheets with excellent press formability the alloying degree must be controlled to reduce the amount of both residual $\zeta$- and $\Gamma$-phases.

Use of the in-situ, fixed detector systems of FIGS. 1a-b and 2a-b enable real-time monitoring of these types of phases, with the source and detectors fixed according to the a-priori knowledge of the particular phases of interest and the position of the sample.

Figure 3A:
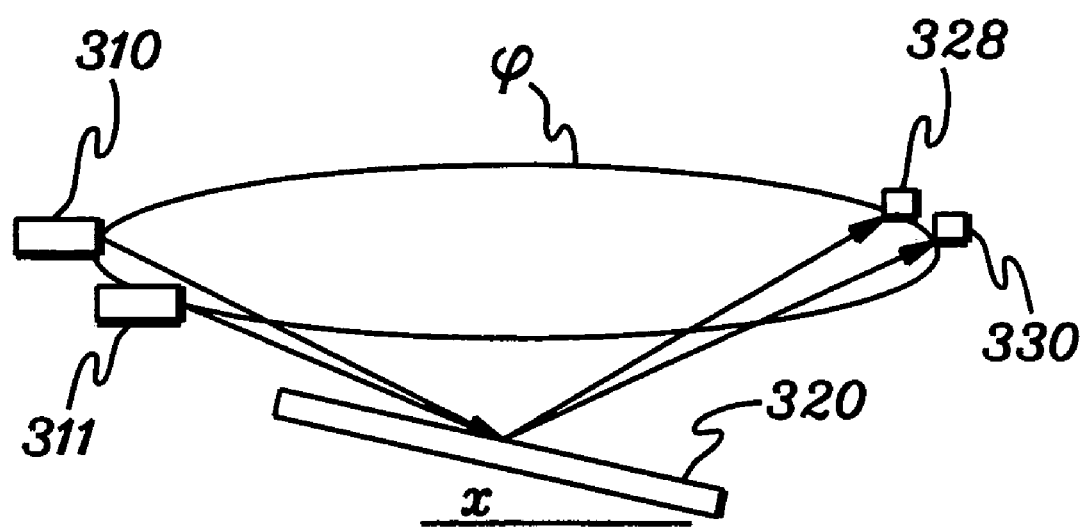
FIGS. 3a-b depict front and top isometric views of a texture measurement, x-ray diffraction system with two sources and two detectors fixed in position at 2 different "φ" directions, in accordance with another aspect of the present invention.
Figure 3B:
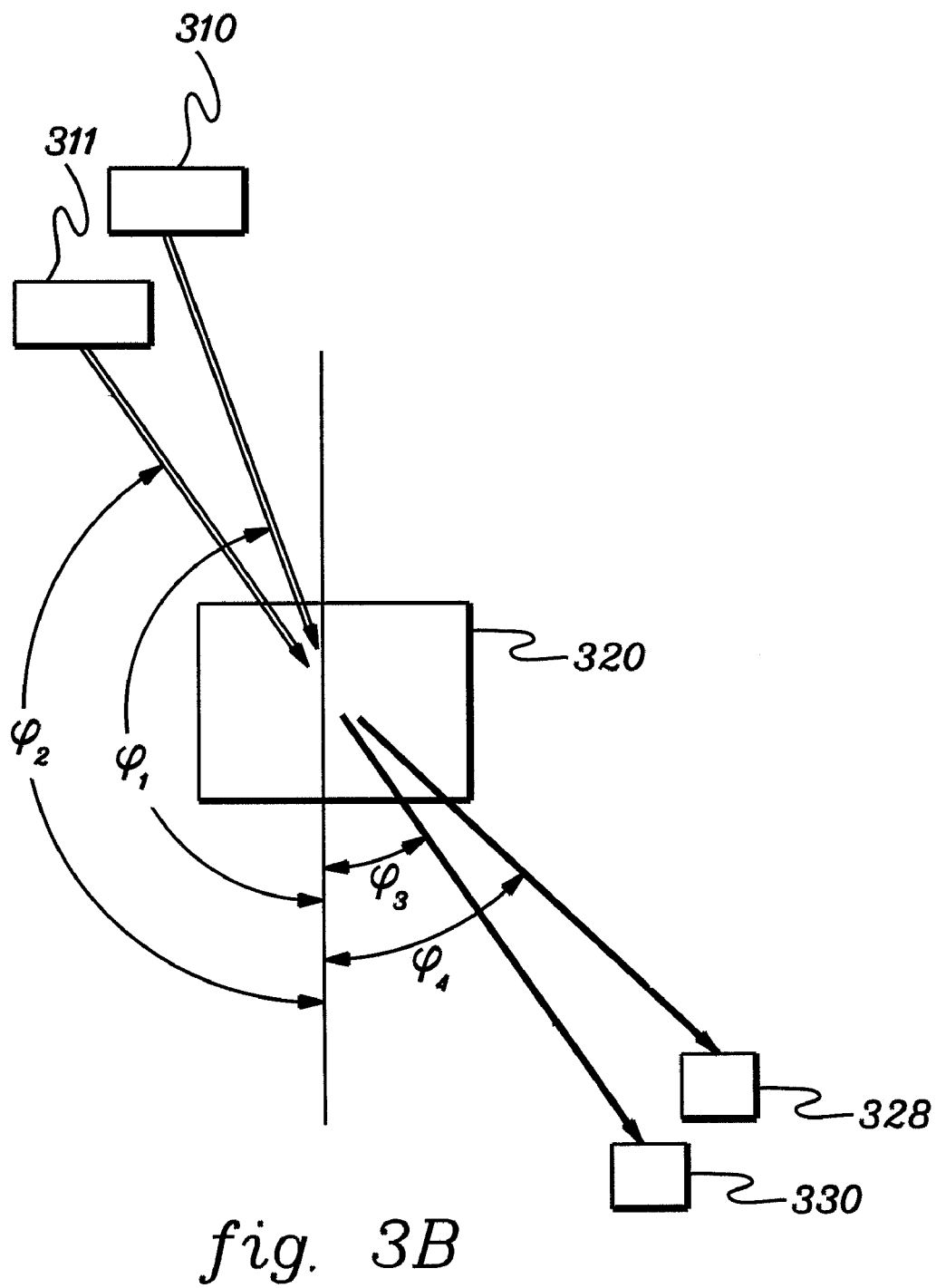

Texture Sensing Embodiments of the Present Invention:

FIGS. 3a-b are schematic front and top isometric views of an embodiment of the present invention optimized for in-situ texture measurements. Here, source detector pairs 310/330 and 311/328 are fixed in respective positions generally along the phi circle, and at a given chi angle to the sample 320.

Texture analysis determines the preferred orientation of the crystallites in polycrystalline aggregates. What is conventionally required is determining the complete orientation distribution of the crystallites. This usually requires systematic changes in the angular orientation of the sample in chi and phi to collect the diffraction data to produce a pole figure plot. A pole figure plot is obtained by measuring the diffraction intensity of a specific plane (for example, [111]

plane) at various settings of the chi and phi angles. Pole figures are convenient illustrations of the constructive interference formed by the diffraction patterns associated with the phases of interest (here, known a-priori). Each constructive interference spot, called a diffraction peak, occurs at a specific location on a specific circle (of varying phi angles) of constant 2-theta angle, where different diffracting planes will produce diffraction peaks at different 2-theta angles. In the ideal case, in which all grains are perfectly aligned with respect to one another, the diffraction peaks appear as dots. In the worst case, in which all the grains are randomly oriented with respect to one another, the diffraction peaks appear as solid rings that occur along the curves of constant 2θ-angle. In the typical case, in which there is a substantial degree of in-plane grain misalignment within the thin film, diffraction peaks appear as elongated spots.

In accordance with the present invention, fixed sources and detectors are used to make this texture measurement without rotation of the sample in the chi or phi directions. In FIGS. 3a-b, the source detector pair 310/330 is fixed at opposing phi angles $\phi_1$ and $\phi_3$, and the source/detector pair 311/328 is fixed at opposing phi angles $\phi_2$ and $\phi_4$.

This configuration is somewhat analogous to the phase monitor embodiments of FIGS. 1a-b and 2a-b, and may also employ the same components (collimating beams, angular filters), however, here there is a source for each detector, and the positions are fixed along the phi direction, though they can also be fixed along the chi and theta directions also.

One application of this configuration could be superconductor tape texture sensing, in which the location of the diffraction peaks is known a-priori, and the source/detector pairs are fixed in the requisite regions to make the particular texture measurement of interest. This application is discussed in greater detail in the commonly assigned provisional patent application entitled "METHOD AND SYSTEM FOR X-RAY DIFFRACTION MEASUREMENTS USING AN ALIGNED SOURCE AND DETECTOR ROTATING AROUND A SAMPLE SURFACE" filed as attorney docket number 0444.070(P) on Jul. 22, 2003, incorporated by reference herein in its entirety. In that application, scanning was proposed to determine a continuous curve of texture measurements. Here, fixed source/detector pairs, e.g., one pair at the orientation corresponding to the peak, and another at the background, could be used to make a similar measurement, assuming the location of the peak is known a-priori to some reasonable degree of accuracy.

In-Situ Examples:

As discussed above, the present invention has particular applicability to certain in-situ environments, where the sample resides in its native state, or in a state of production along a production line.

Figure 4:
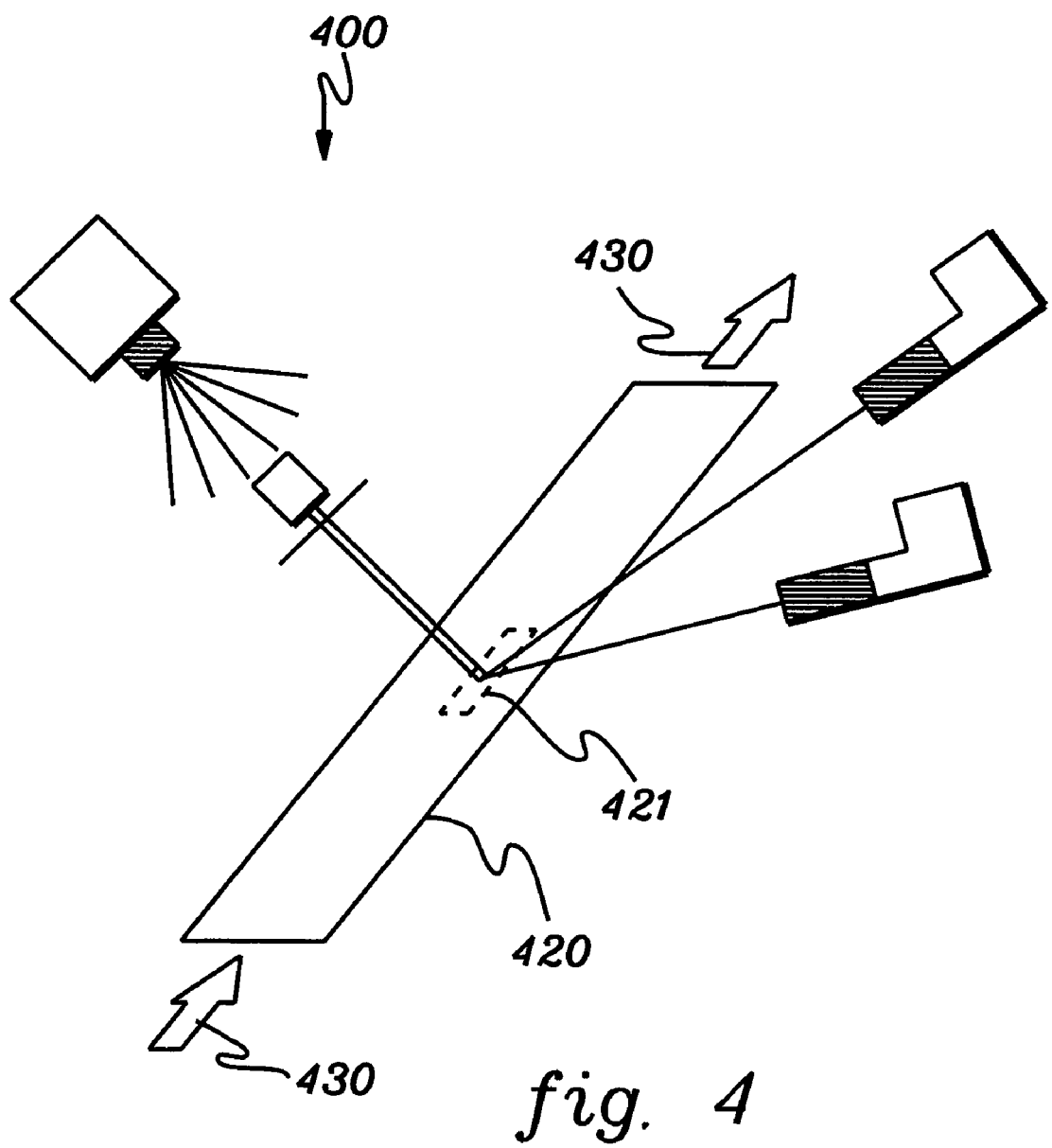
FIG. 4 depicts an in-situ, x-ray diffraction system with fixed detectors monitoring a moving sample in a production setting.

FIG. 4 depicts an "in-line" version of an in-situ system 400, coupled directly to a production line, and analyzing an area 421 of material 420 as it exists (possibly moving) in the production line, in a substantially predictable state (especially with respect to the theta, phi and chi angles discussed above). This type of environment may be applicable to the steel example discussed above, where steel sheets under production are moving along a movement path 430, or a texture measurement example discussed above, where superconductive tape is moving past the in-situ system. While the system may gather diffraction data through an area of the material, as a function of translation rate and sampling duration, the material could be stopped and discrete points and the measurement made at each point. However, continuous data sampling along an area of the material during continuous movement may be desirable for processing.

Figure 5:
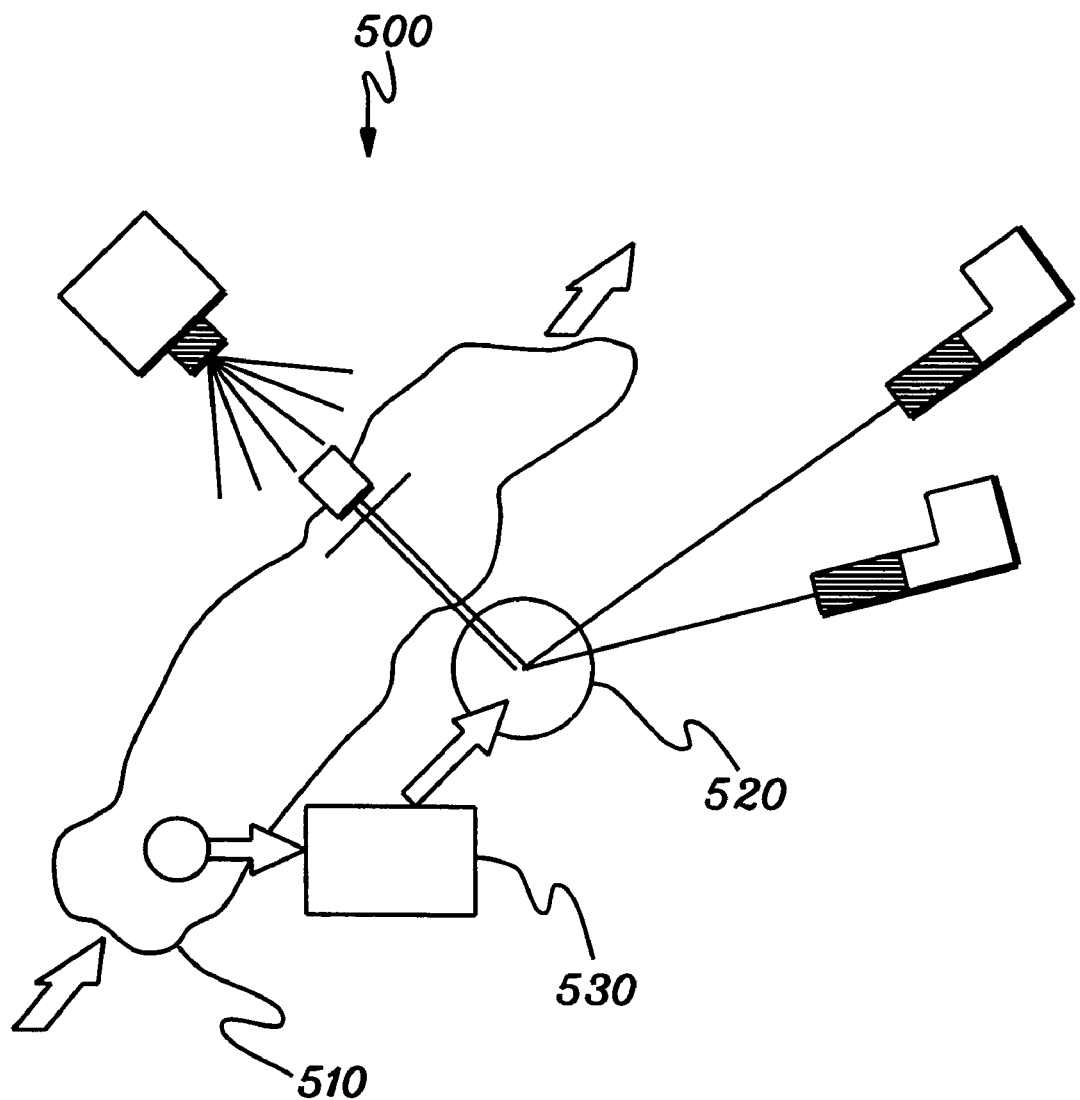
FIG. 5 depicts an in-situ, x-ray diffraction system with fixed detectors measuring a sample in a production bypass path.

FIG. 5 depicts an "at-line" version of an in-situ XRD system 500, proximate to ("at") a production line, and analyzing a sample 520 of material 510 as it exists (possibly moving) in the production line, in a substantially predictable state (especially with respect to the theta, phi and chi angles discussed above). Minimal sample handling and preparation is performed (530), and the sample exists under measurement by system 500 essentially as it existed in the production line.

Other "in-situ" environments are contemplated by the present invention. For example, an "on-site" system which can be portably transported to a site at which the sample resides in a substantially predictable state (e.g., an ore mine where certain characteristics of the samples are of interest; or forensic scenes where certain known materials are being sought).

Low Power Source/Collimating Optic Combination Examples:

As discussed above, the ability to provide an in-situ analysis capability depends to a large extent upon source/optic technology which can tolerate the environmental and portability requirements of those environments. In that regard, certain source and optic technology formerly disclosed and assigned to the assignee of the present invention can be optimized for use in in-situ environments, as discussed below with respect to FIGS. 6a-c.

Figure 6A:
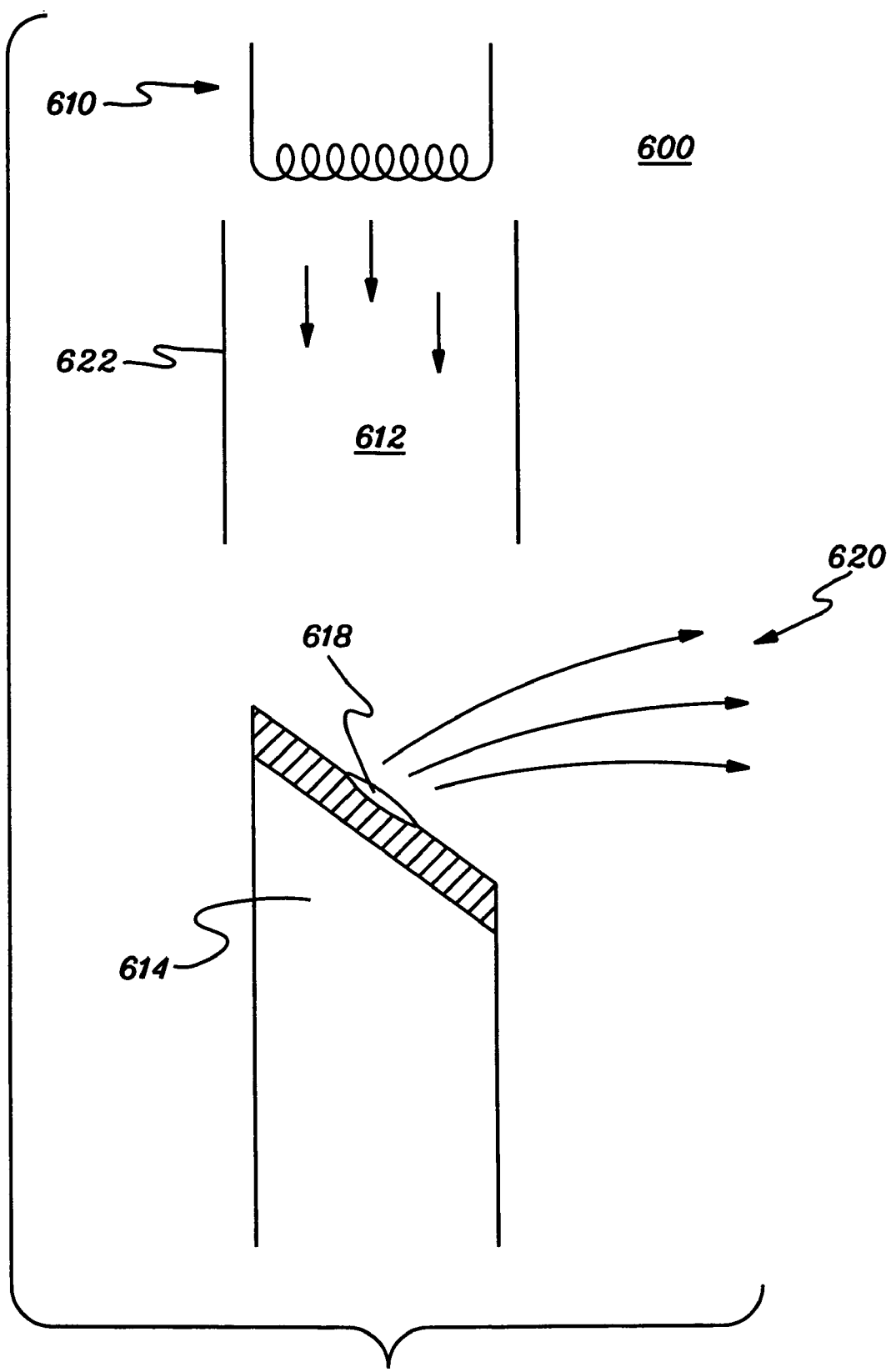
FIGS. 6a-c depict an electron bombardment source, polycapillary collimating optic, and source/optic combination optimized for use in the x-ray diffraction system of the present invention.

Referring now to FIG. 6a, the basic elements of a typical compact, electron-bombardment x-ray source 600 are shown. Electron gun/filament 610 is heated (by applying a voltage) to a temperature such that electrons 612 are thermally emitted. These emitted electrons are accelerated by an electric potential difference to anode 614, which is covered with target material, where they strike within a given surface area of the anode, called the spot size 618. Divergent x-rays 620 are emitted from the anode as a result of the collision between the accelerated electrons and the atoms of the target. To control the spot size, electromagnetic focusing means 622 may be positioned between filament 610 and anode 614. X-ray sources with spot sizes of 2 microns or less are available commercially. However, as the electron spot size decreases, so does the production of x rays.

Figure 6B:
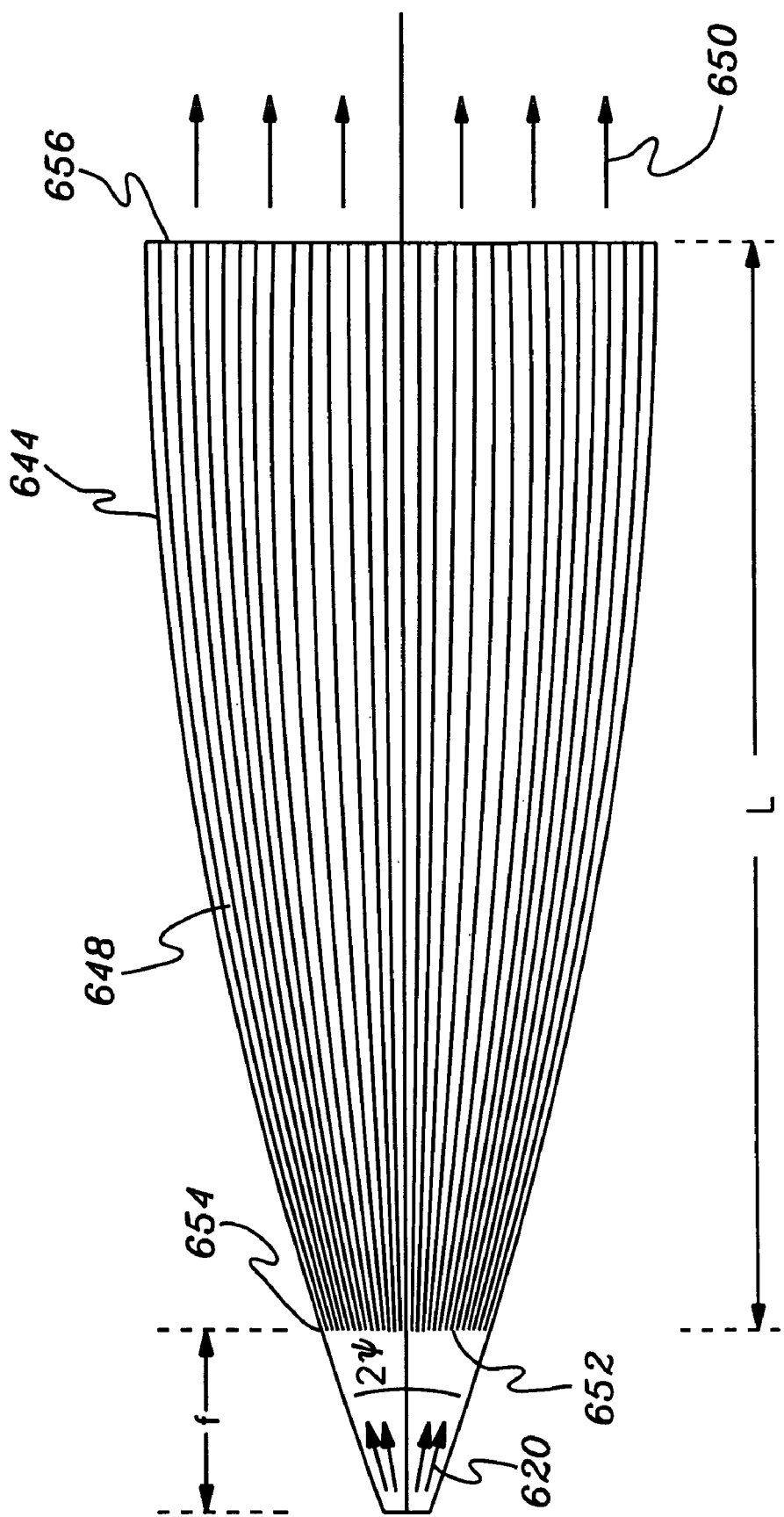

With reference to FIG. 6b, producing a high intensity, small diameter x-ray beam requires both the small spot x-ray source 600, coupled to a monolithic, polycapillary collimating optic 644. These two components are usually separated by a distance f, known as the focal distance. The optic 644 comprises a plurality of hollow glass capillaries 648 fused together and shaped into configurations which allow efficient capture of divergent x-ray radiation 620 emerging from x-ray source 600. In this example the captured x-ray beam is shaped by the optic into a substantially parallel beam 650. The channel openings 652 located at the optic input end 654 are roughly pointing at the x-ray source. The ability of each individual channel to essentially point at the source is of significant importance for several reasons: 1) it allows the input diameter of the optic to be sufficiently decreased, which in turn leads to the possibility of smaller optic output diameters; and 3) it makes efficient x-ray capture possible for short optic to source focal lengths. The diameters of the individual channel openings 652 at the input end of the optic 654 may be smaller than the channel diameters at the output end of the optic 656.

This type of optic redirects the otherwise divergent x-rays from the source into the output, parallel beam 650. This not only ensures maximal efficiency, but provides some immunity to displacement of the sample under study in the x-ray diffraction systems discussed above.

Figure 6C:
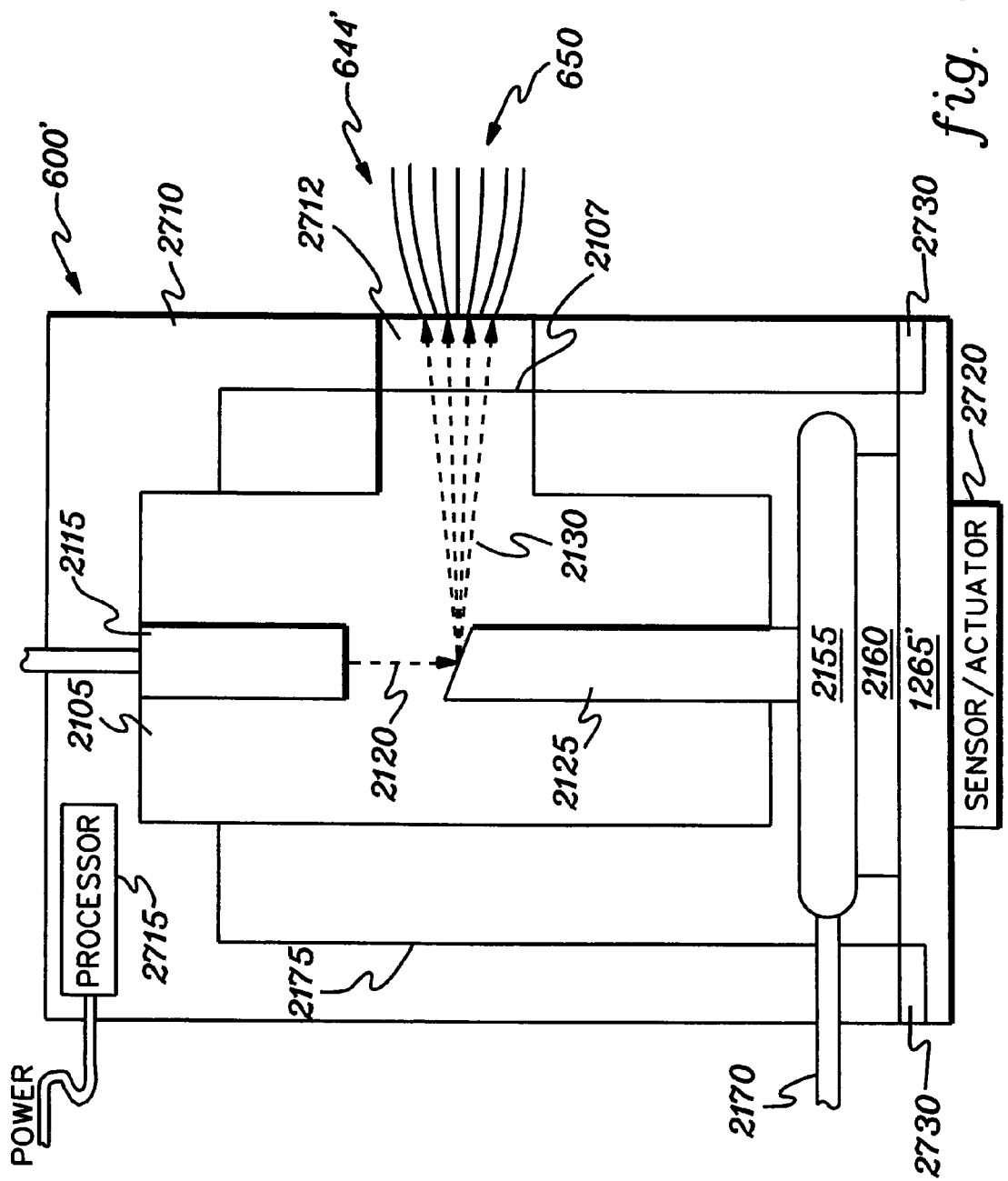

FIG. 6c illustrates in cross-section an elevational view of one embodiment of an x-ray source/optic assembly particularly suited for the diffraction systems of the present invention. X-ray source/optic assembly includes an x-ray source 600' and an output optic 644'—similar to those discussed above with respect to FIGS. 6a-b. Optic 644' is aligned to x-ray transmission window 2107 of vacuum x-ray tube 2105. X-ray tube 2105 houses electron gun/filament 2115 arranged opposite to high voltage anode 2125. When voltage is applied, electron gun 2115 emits electrons in the form of an electron stream 2120 (as described above). HV anode 2125 acts as a target with respect to a source spot upon which the electron stream impinges for producing x-ray radiation 2130 for transmission through window 2107 and collection by optic 644'.

Anode 2125 may be physically and electrically connected to a base assembly which includes a conductor plate 2155 that is electrically isolated from a base plate 1265' via a dielectric disc 2160. A high voltage lead 2170 connects to conductive plate 2155 to provide the desired power level to anode 2125. The electron gun 2115, anode 2125, base assembly 1265'/2160/2155 and high voltage lead 2170 may be encased by encapsulant 2175 all of which reside within a housing 2710. (However, dielectric disk 2160 functions to remove excess heat from the assembly, in one embodiment negating the need for any special cooling encapsulants). Housing 2710 includes an aperture 2712 aligned to x-ray transmission window 2107 of x-ray tube 2105. In operation, x-ray radiation 2130 is collected by optic 644', and in this example, redirected into a substantially parallel beam 650.

A control system may also be implemented within x-ray source assembly 600'. This control system includes, for example, a processor 2715, which is shown embedded within housing 2710, as well as one or more sensors and one or more actuators (such as sensor/actuator 2720 and actuator 2730), which would be coupled to processor 2715. This control system within x-ray source assembly 600' includes functionality to compensate for, for example, thermal expansion of HV anode 2125 and base assembly 1265'/2160/2155 with changes in anode power level in order to maintain an alignment of x-rays 2130 with respect to optic 644'. This enables the x-ray source assembly 600' to maintain a spot size with stable intensity within a range of anode operating levels.

This parallel beam production and transmission can be effected by the polycapillary collimating optics and optic/source combinations such as those disclosed in commonly assigned, X-Ray Optical Systems, Inc. U.S. Pat. Nos. 5,192,869; 5,175,755; 5,497,008; 5,745,547; 5,570,408; and 5,604,353; U.S. Provisional Applications Ser. Nos. 60/398,968 (filed Jul. 26, 2002 and perfected as PCT Application PCT/US02/38803) and 60/398,965 (filed Jul. 26, 2002 and perfected as PCT Application PCT/US02/38493)—all of which are incorporated by reference herein in their entirety.

Figure 7:
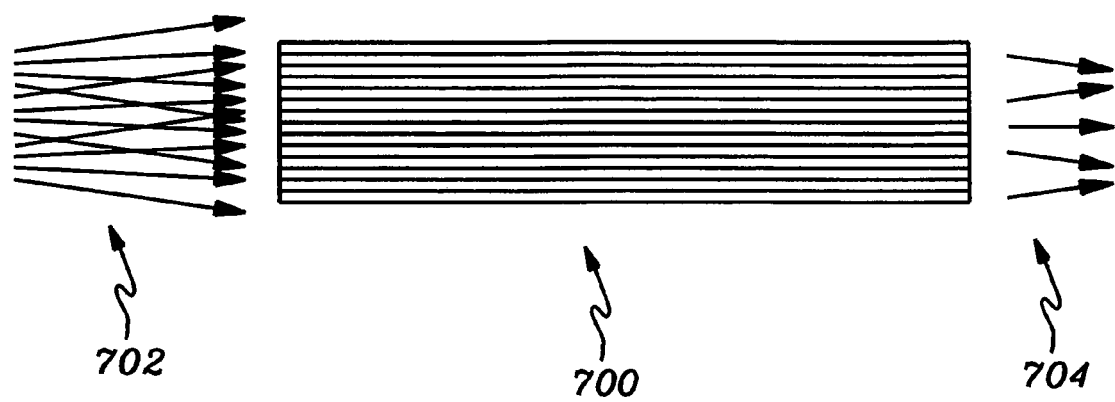
FIG. 7 depicts an exemplary, angular filter used in combination with the fixed detector(s) in accordance with another aspect of the present invention.

Angular Filter Technology:

FIG. 7 depicts a typical polycapillary angular filter 700 useful in the present invention fabricated from a large number of small glass capillaries. Since the refractive index of x-rays in glass is slightly less than unity, total reflection occurs when x-rays 702 are incident on a smooth glass surface at a small incident angle. The critical angle for total external reflection is inversely proportional to the x-ray energy and for 30 keV x-rays is about one milliradians (~0.05 degrees). X-rays incident at angles less than the critical angle can then be transmitted 704 through hollow glass capillaries.

By limiting angles of critical energy reaching the detector, scattering can be controlled from unwanted angles, thus controlling the area of the sample from which energy is detected. As discussed above, controlling the critical angle and other design parameters of the angular filters according to the peak widths of interest is useful in the present invention, to ensure that the maximal energy from the peak(s) is collected, while also limiting the amount of noise received from off-peak areas. The angular filters should be pointed at the sample area of interest.

Other types of angular filters are possible, including soller slits, multi-channel plates, etc. One- or two-dimensional alternatives can also be used.

Figure 8:
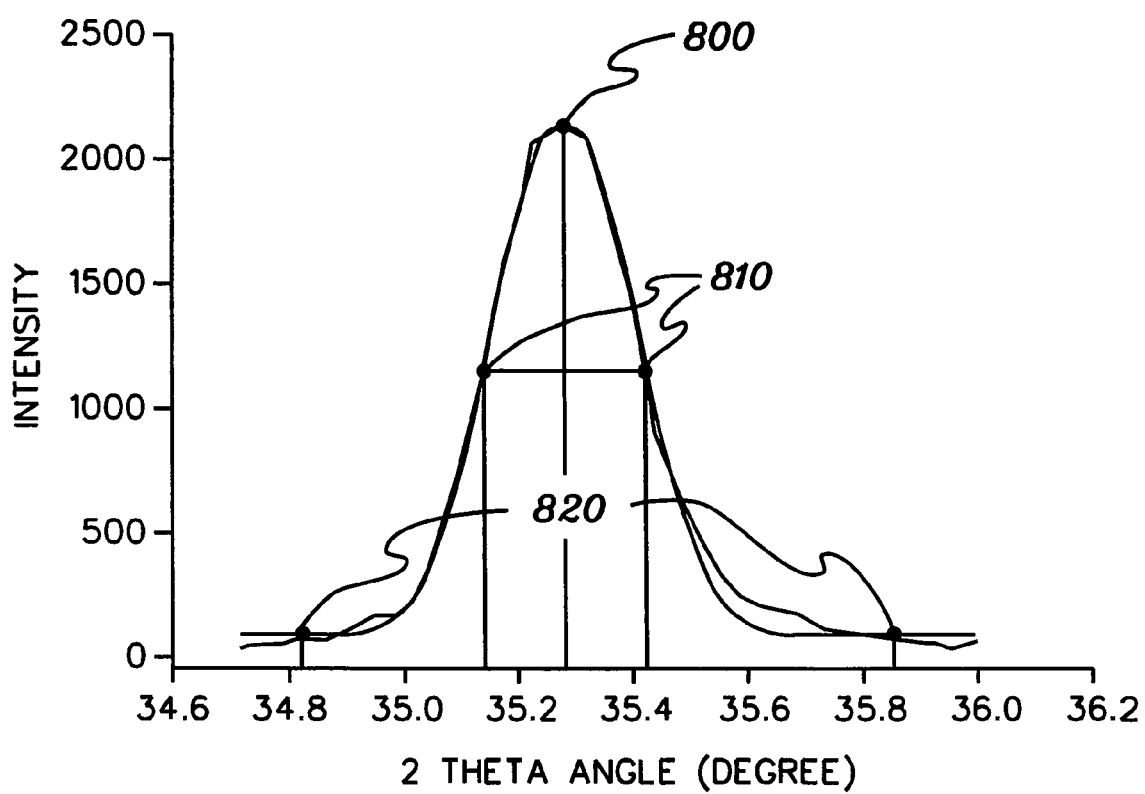
FIG. 8 depicts a typical "2θ" angle scan, and the potential orientation of fixed detectors, in accordance with the present invention.

Scanned Curves and the Derivation of Fixed Source/Detector Positions:

FIG. 8 depicts a sample diffraction curve derived (e.g., in a laboratory) from scanning a source and detector in the 2-theta direction across a representative sample of interest. Though the 2-theta position is shown, similar curves are derived in diffraction practices generally, from which fixed detector locations can be derived. Upon derivation of this curve, and in accordance with the present invention, fixed sources and/or detectors can be placed at the noted angular positions 800, 810 and 820 in accordance with the present invention. Ideally, only a single "peak" detector may be necessary at peak 800, however, the ability to place detectors at other points in the curve (e.g., the full-width half max position 810) and/or at the background positions 820, will provide more reliable results. In a preferred embodiment of the present invention, a single peak detector is used, and a single background detector is used, close to the diffraction angle of the peak (to ensure the same general type of diffraction conditions are collected) but far enough into the noise to ensure a distinctive measurement between the peak and noise—thereby providing an accurate peak magnitude measurement. But three detectors can be used (peak, half peak and noise); or five detectors (peak, half peak—both sides, and noise—both sides); or more detectors; or any desired mix of detectors or source/detector pairs.

This invention can also be used for other applications like in-situ strain and stress measurements by collecting, in real time, the diffraction peak profiles, using detectors at fixed positions as discussed above. To obtain high quality data for measurement with high precision, linear detector or even area detectors could be used as well for any of the above-described detectors.

The processing portions of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An x-ray diffraction apparatus for measuring a known characteristic of a sample of a material in an in-situ state, comprising:
   an x-ray source for emitting substantially divergent x-ray radiation;
   a collimating optic disposed with respect to the x-ray source for producing a substantially parallel beam of x-ray radiation by receiving and redirecting the divergent paths of the divergent x-ray radiation toward the sample, the collimating optic employing multiple total external reflections as its primary transmission technique; and
   first and second point x-ray detectors for collecting radiation emitted from the sample, wherein the first x-ray detector is fixed in position to measure a diffraction peak determined according to the a-priori knowledge, and wherein the second x-ray detector is fixed in position to measure off the diffraction peak determined according to the a-priori knowledge;
   wherein the source and detectors are fixed, during operation thereof, in positions relative to each other and in at least one dimension relative to the sample according to a-priori knowledge about the known characteristic of the sample; and
further comprising at least one angular filter, having multiple, parallel capillaries employing total external reflection, the at least one angular filter affixed to the first and/or second x-ray detectors for limiting the angles from which the radiation is collected by the respective detector.

2. The apparatus of claim 1, wherein the second x-ray detector is fixed in position to measure substantially noise off the diffraction peak.

3. The apparatus of claim 1, further comprising the sample, wherein the sample requires phase monitoring and the apparatus is adapted to monitor said phase.

4. The apparatus of claim 3, wherein the sample is in a production line and moving past the source and detectors.

5. The apparatus of claim 1, further comprising a second source fixed relative to the second detector, wherein the first source and detector operate as a pair, and the second source and detector operate as a pair.

6. The apparatus of claim 5, further comprising the sample, wherein the sample requires texture monitoring and the apparatus is adapted to monitor said texture.

7. The apparatus of claim 6, wherein the sample is in a production line and moving past the sources and detectors.

8. An x-ray diffraction apparatus for measuring a known characteristic of a sample of a material in an in-situ state, comprising:
   an x-ray source for emitting substantially divergent x-ray radiation;
   a collimating optic disposed with respect to the x-ray source for producing a substantially parallel beam of x-ray radiation by receiving and redirecting the divergent paths of the divergent x-ray radiation toward the sample, the collimating optic employing multiple total external reflections as its primary transmission technique; and
   first and second point x-ray detectors for collecting radiation emitted from the sample, wherein the first x-ray detector is fixed in position to measure a diffraction peak determined according to the a-priori knowledge, and wherein the second x-ray detector is fixed in position to measure off the diffraction peak determined according to the a-priori knowledge;
   wherein the source and detectors are fixed, during operation thereof, in positions relative to each other and in at least one dimension relative to the sample according to a-priori knowledge about the known characteristic of the sample; and
   wherein the collimating optic has a plurality of capillaries and is shaped such that each capillary of the plurality of capillaries essentially points at the x-ray source, and employs multiple total external reflections within the capillaries to shape the divergent x-ray radiation into the substantially parallel beam by receiving and redirecting the divergent paths of the divergent x-ray radiation; and
   further comprising at least one angular filter, having multiple, parallel capillaries employing total external reflection, the at least one angular filter affixed to the first and/or second x-ray detectors for limiting the angles from which the radiation is collected by the respective detector.

9. The apparatus of claim 8, wherein the second x-ray detector is fixed in position to measure substantially noise off the diffraction peak.

10. An x-ray diffraction method for measuring a known characteristic of a sample of a material in an in-situ state, comprising:
    emitting substantially divergent x-ray radiation with an x-ray source;
    producing a substantially parallel beam of x-ray radiation by receiving and redirecting the divergent paths of the divergent x-ray radiation toward the sample with a collimating optic which employs multiple total external reflections as its primary transmission technique;
    collecting radiation emitted from the sample with first and second x-ray detectors, wherein the first x-ray detector is fixed in position to measure a diffraction peak determined according to the a-priori knowledge, and wherein the second x-ray detector is fixed in position to measure off the diffraction peak determined according to the a-priori knowledge;
    wherein the source and detectors are fixed, during operation thereof, in positions relative to each other and in at least one dimension relative to the sample according to a-priori knowledge about the known characteristic of the sample; and
further comprising using at least one angular filter, having multiple, parallel capillaries employing total external reflection, the at least one angular filter affixed to the first and/or second x-ray detectors for limiting the angles from which the radiation is collected by the respective detector.

11. The method of claim 10, wherein the second x-ray detector is fixed in position to measure substantially noise off the diffraction peak.

12. The method of claim 10, wherein the sample requires phase monitoring, the method further comprising monitoring said phase.

13. The method of claim 12, further comprising moving the sample in a production line past the source and detectors.

14. The method of claim 10, further comprising emitting substantially divergent x-ray radiation with a second source fixed relative to the second detector, wherein the first source and detector operate as a pair, and the second source and detector operate as a pair.

15. The method of claim 14, wherein the sample requires texture monitoring, the method further comprising monitoring said texture.

16. The method of claim 15, further comprising moving the sample in a production line past the source and detectors.

17. An x-ray diffraction method for measuring a known characteristic of a sample of a material in an in-situ state, comprising:
   emitting substantially divergent x-ray radiation with an x-ray source;
   producing a substantially parallel beam of x-ray radiation by receiving and redirecting the divergent paths of the divergent x-ray radiation toward the sample with a collimating optic which employs multiple total external reflections as its primary transmission technique;
   collecting radiation emitted from the sample with first and second x-ray detectors, wherein the first x-ray detector is fixed in position to measure a diffraction peak determined according to the a-priori knowledge, and wherein the second x-ray detector is fixed in position to measure off the diffraction peak determined according to the a-priori knowledge;
   wherein the source and detectors are fixed, during operation thereof, in positions relative to each other and in at least one dimension relative to the sample according to a-priori knowledge about the known characteristic of the sample;
   wherein the collimating optic has a plurality of capillaries and is shaped such that each capillary of the plurality of capillaries essentially points at the x-ray source, and employs multiple total external reflections within the capillaries to shape the divergent x-ray radiation into the substantially parallel beam by receiving and redirecting the divergent paths of the divergent x-ray radiation; and
   further comprising using at least one angular filter, having multiple, parallel capillaries employing total external reflection, the at least one angular filter affixed to the first and/or second x-ray detectors for limiting the angles from which the radiation is collected by the respective detector.

18. The method of claim 17, wherein the second x-ray detector is fixed in position to measure substantially noise off the diffraction peak.

* * * * *